United States Patent [19]

Barnes

[11] 4,340,818

[45] Jul. 20, 1982

[54] SCANNING GRID APPARATUS FOR SUPPRESSING SCATTER IN RADIOGRAPHIC IMAGING

[75] Inventor: Gary T. Barnes, Birmingham, Ala.

[73] Assignee: The Board of Trustees of the University of Alabama, Birmingham, Ala.

[21] Appl. No.: 149,754

[22] Filed: May 14, 1980

[51] Int. Cl.³ .................................................. H01J 35/16
[52] U.S. Cl. ........................................ 250/509; 250/508
[58] Field of Search ............... 250/508, 509, 505, 511, 250/512, 513

[56] References Cited

U.S. PATENT DOCUMENTS

| | | | |
|---|---|---|---|
| 1,164,987 | 12/1915 | Bucky . | |
| 1,484,663 | 2/1924 | Mutscheller | 250/509 |
| 1,567,833 | 12/1925 | Bucky | 250/509 |
| 2,511,853 | 6/1950 | Kaiser | 250/509 |
| 2,665,387 | 1/1954 | Bartow | 250/508 |
| 3,919,559 | 11/1975 | Stevens | 250/508 |
| 3,997,794 | 12/1976 | York et al. | 250/511 |
| 4,096,391 | 6/1978 | Barnes | 250/505 |
| 4,126,786 | 11/1978 | LeMay et al. | 250/44 ST |

FOREIGN PATENT DOCUMENTS 778803 3/1935 France .

OTHER PUBLICATIONS

Potter, "The Bucky Diaphragm Principle Applied to Roentgenography", Am. J. Roentgenol, vol. 7, pp. 292–295, 1920.
Brezovich et al., "A New Type of Grid", Med. Phys., vol. 4, No. 5, Sep./Oct. 1977, pp. 451–453.
Barnes et al., "The Scanning Grid: A Novel and Effective Bucky Movement", Radiology, vol. 135, pp. 765–767, Jun. 1980.

Primary Examiner—Alfred E. Smith
Assistant Examiner—Carolyn E. Fields
Attorney, Agent, or Firm—Oblon, Fisher, Spivak, McClelland & Maier

[57] ABSTRACT

A scanning grid apparatus exhibiting high primary and low secondary X-Ray transmission of X-Ray radiation emitted from an X-Ray source defining a focal spot, including at least one scanning grid provided with top and bottom pairs of opposed grid slat retainers disposed in parallel planes. Pivotably attached between the top pair of retainers is a plurality of radiopaque linear or wavy grid slats separated at predetermined distances in the plane of the top pair of retainers. The bottom pair of retainers includes spacers for maintaining the grid slats separated predetermined distances within allowable limits in the plane of the bottom pair of retainers. The separation distances provided by the bottom pair of retainers is chosen as the geometric projection of the separation distances in the plane of the top pair of retainers from the source focal spot to the plane of the bottom pair of retainers, such that each of the grid slats is focused on the focal spot of the X-Ray source. The pairs of grid slat retainers are mechanically coupled to the source focal spot by means of a slotted linkage arm capable of moving the pairs of grid slat retainers linearly in the direction transverse to the plural grid slats to blur out and render invisible slat shadows which would otherwise appear on an image receptor, while nevertheless maintaining the grid slats focused on the source focal spot to reduce primary radiation cut-off. A pair of scanning grids in which the grid slat retainers of the respective grids are arranged orthogonally may be staggered between a subject and an X-ray image receptor to further suppress secondary radiation.

11 Claims, 9 Drawing Figures

SCANNING GRID APPARATUS FOR SUPPRESSING SCATTER IN RADIOGRAPHIC IMAGING

BACKGROUND OF THE INVENTION

1. Field of the Invention

This Application relates to Bucky-type grids used in x-ray radiology, and more particularly to an improved scanning grid apparatus exhibiting high primary and low secondary or scattered radiation transmission.

2. Description of the Prior Art

A conventional Bucky grid consists of an array of radiopaque (usually lead) foil strips which are separated by strips of radiolucent spacing material. The array is positioned between an object being irradiated and an image receptor so that the image-forming x-rays from the focal spot of the x-ray source see only the edges of the foil strips and the majority pass through the radiolucent spacers. A significant portion (typically 30–45%), however, of the image-forming or primary x-rays are attenuated by the lead strips and interspacing material. Scattered x-rays are omitted, on the other hand, from the patient in all directions and the majority of these that are emitted toward the image receptor do not have a straight line path through the radiolucent spacers to the image receptor and are therefore absorbed (typically 85–95%) in the lead.

Typically, the thickness of lead foil strips is 2 mils and the thickness of interspace material varies from 8 to 15 mils, depending on the number of grid strips or lines per inch. The geometry of the conventional grid is depicted in FIG. 1. The ratio of the height (h) of the lead strips to the interspace material thickness (D) or h/D is defined in the literature as the grid ratio (r). Typical grid ratio values vary from 4/1 to 16/1. For a given number of grid lines per inch as one increases the height (h) of the lead strips or grid ratio, the scattered radiation transmitted by the grid decreases. However, two factors limit this in practice. These factors are the increased attenuation by the interspace material (usually cotton fiber or aluminum) of the primary X-Ray, i.e. non-scattered, beam and increased difficulty in aligning and maintaining alignment of the grid with the primary X-Ray beam.

The lead strip arrangements commonly employed in different types of grids are illustrated in FIGS. 1 and 2 with the linear focused grid being the most widely used. The advantage of a focused grid compared to a linear parallel grid is that there is no grid cut-off at the edges of the grid as there is with a parallel grid. Grid cut-off is a loss of primary radiation resulting from the primary X-Rays not being properly aligned with the lead strips. Another type of grid that is occasionally employed, that is not depicted in FIGS. 1 and 2, is a crossed grid. It is made up of two orthogonal superimposed linear grids which have the same focus distance.

One disadvantage of using a grid is that a pattern of clear (white) lines is cast onto the film. This pattern of grid lines can be distracting to the radiologist, especially if the lines are thick and widely spaced. The common solution to this problem is to move the grid sideways (perpendicular to the grid strips) across the film during an exposure. The shadows of the grid strips are blurred out and are, therefore, not visible. However, this blurring movement results in decreased primary transmission, since the x-ray source cannot remain aligned with the focal line of the grid while it is being moved. This decrease in primary transmission associated with the grid blurring movement is more pronounced for high ratio grids.

Since the issuance of the original Bucky patent (U.S. Pat. No. 1,164,987), further scatter suppression techniques have been disclosed in the patent literature, as, for example, evidenced in U.S. Pat. No. 1,484,663 to Mutscheller, and the recent U.S. Pat. No. 4,126,786 to LeMay et al. Mutscheller discloses an x-ray filter for preventing secondary x-rays from reaching an object to be operated upon by primary x-rays. His filter includes, among other things, a grid and means for moving the grid bodily while in action, the grid being provided with slats each journaled to turn slightly upon an axis of its own, and to provide means for thus turning the slats, in order to maintain each slat exactly edgewise relatively to the position of the target, and for coordinating the turning movement of the slats with the bodily movement of the grid. LeMay et al discloses a computerized axial tomography (CAT) scanner of the type in which a fan of radiation affects a rotational scan and the detectors are fixedly positioned, wherein post-patient collimation is achieved by means of plural plates hingedly attached adjacent the detectors for defining primary x-ray paths to the detectors and shielding the detectors from scattered radiation. The LeMay et al post-patient collimator is tiltable in the plane of the patient's radiation slice to permit radiation, originating from a range of positions to impinge upon the detectors. According to LeMay et al, the collimator is constructed of a plurality of plate members protruding from the detectors towards the patient position, wherein a pair of the plate members flank each individual detector and wherein the plate members are hinged at their ends adjacent the detectors to permit tilting to occur.

In French Pat. No. 778,803 is disclosed a secondary radiation absorbing grid in which the individual grid members are implemented by means of a variety of zig-zag, wavy, and/or crinkle grid septa shapes. See also Brezovich and Barnes, "A New Type of Grid", MED. PHYS. 4:451–453, September/October 1977.

SUMMARY OF THE INVENTION

Accordingly, one object of this invention is to provide a novel scanning grid which is simple to fabricate and which exhibits improved performance relative to the prior art Bucky-type grids.

Another object of this invention is to provide a novel scanning grid to be disposed between a subject being irradiated by x-rays emitted from a x-ray source and an x-ray sensitive object, which exhibits improved transmissivity of primary x-rays passing through the subject.

Yet another object of this invention is to provide a novel scanner of the above-noted type which exhibits reduced cut-off of primary radiation which penetrates the subject being irradiated.

A further object is to provide a new and improved scanning grid of the above-noted type which exhibits reduced scatter radiation penetration.

Yet another object of this invention is to provide a new and improved scanning grid as noted above, which employs higher grid ratios than heretofore possible to attain reduced scatter radiation penetration.

These and other objects are achieved according to the invention by providing a new and improved scanning grid apparatus exhibiting high primary and low secondary x-ray transmission of x-ray radiation emitted from an x-ray source defining a focal spot, the emitted radiation passing through a subject, the scanning grid apparatus, and then on to an x-ray sensitive image receptor in that order, including at least one scanning grid provided with first and second pairs of opposed grid slat retainers disposed in parallel planes, with the first pair located between the subject and the second pair. Pivotably attached between the first pair of retainers is a plurality of radiopaque grid slats separated at predetermined distances. The second pair of retainers includes spacers for maintaining the grid slats separated at predetermined distances within predetermined limits in the plane of the second pair of retainers. The separation distances provided by the second pair of retainers is selected as the geometric projection from the focal spot of the separation distance provided by the first pair of retainers such that each of the grid slats is focused on the focal spot of the x-ray source. The pairs of grid slat retainers are then coupled to the x-ray source focal spot by means of, for example, a slotted linkage arm which moves the pairs of grid slat retainers linearly in a direction transverse to the plural grid slats to blur out and render invisible slat shadows which would otherwise appear on an image receptor, while nevertheless maintaining the grid slats focused on the x-ray source, thereby maximizing primary transmission. In the event that the x-ray source is maintained stationary, then both pairs of grid slat retainers are moved linearly in a direction transverse to the plural grid slats at distances proportional to the separation distance of the respective pairs of retainers from the focal spot. If desired, focus can be maintained when the x-ray source to image receptor distance is varied by changing the separation distance between the first and second set of retainers. The position of the x-ray source can lie along a line parallel to the planes of the retainers and transverse to the grid slats allowing for oblique as well as normal incident on the image receptor of the central ray. In a tomographic source and image receptor movement, the bottom pair of grid slat retainers can remain stationary, while the top pair is linearly moved by the linkage arrangement maintaining grid slat force.

In alternative embodiments, special measures are taken to minimize transmission of secondary radiation parallel to the grid slats. In one such embodiment, each of the grid slats is provided with a wavy cross-section with the period of the waves diverging from the first pair of retainers to the second pair of retainers in convergence on the focal spot. Preferably in this embodiment the wavy grid slats are intermeshed to further obstruct secondary scatter radiation.

In another embodiment, two scanning grids arranged with the grid slats thereof orthogonally disposed with respect to each other are employed, with the grid slat retainers of both the scanning grids mechanically, electronically, hydraulically, or in some alternative manner coupled to the focal spot in order to assure continuous grid slat focusing on the focal spot.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 7b is a cross-sectional view taken along the lines 7b—7b of FIG. 7a illustrating the relative intermeshing of adjacent wavy-grid slats in the embodiment shown in FIG. 7a.

DESCRIPTION OF THE PREFERRED EMBODIMENTS

Figure 3:
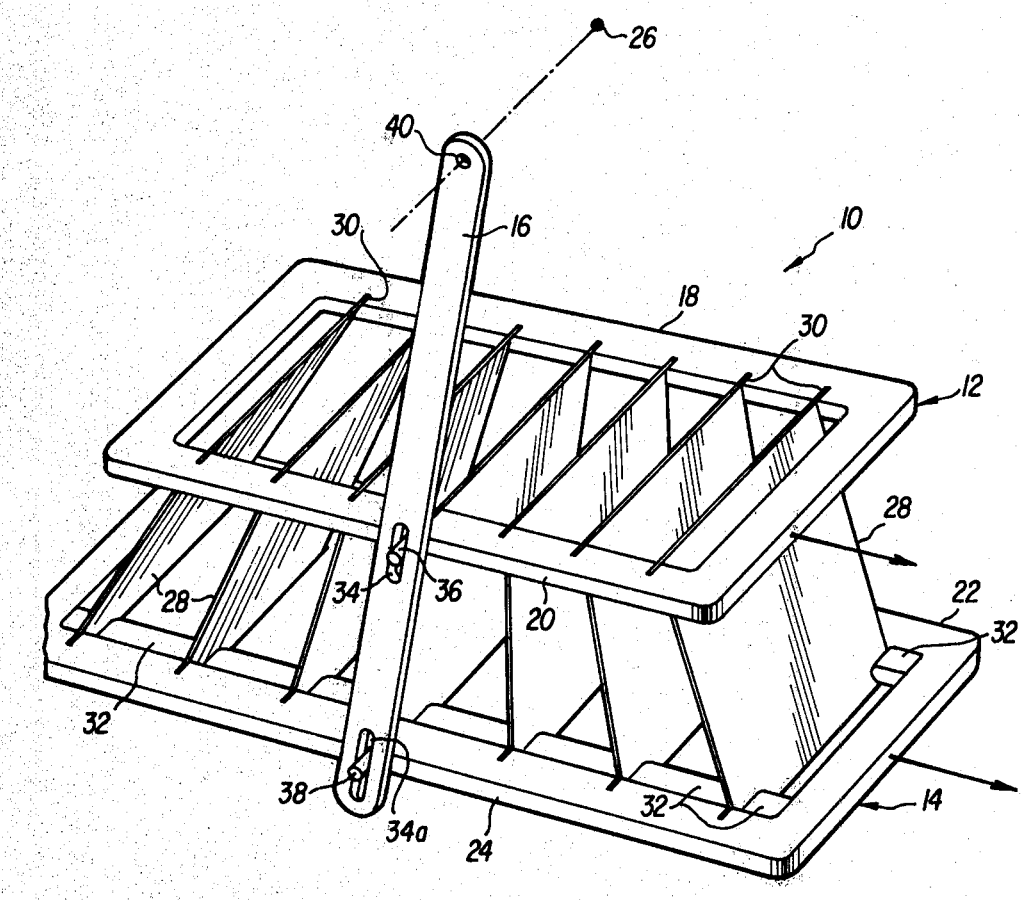
FIG. 3 is a perspective view of a first embodiment of a scanning grid apparatus according to the invention.

Referring now to the drawings, wherein like reference numerals designate identical or corresponding parts throughout the several views, and more particularly to FIG. 3 thereof, there is shown a scanning grid 10 of one embodiment of the invention, constructed of an upper support plate 12, a lower support plate 14, and a linkage arm 16. The upper support plate 12 includes a pair of opposed grid slat retainers 18 and 20, while the lower support plate 14 likewise includes a pair of opposed grid slat retainers 22 and 24. The upper and lower support plates 12 and 14 and the associated grid slat retainers (18, 20) and (22, 24) are arranged in parallel planes, which are parallel to the plane of a subject (not shown) being irradiated by an x-ray source characterized by a point source focal spot indicated as 26.

Suspended between parallel opposed grid slat retainers 18 and 20 and pivotably attached thereto are plural radiopaque grid slats 28, each supported by pins 30 coupled to opposed grid slat retainers 18 and 20 such that the grid slats 28 are suspended from the retainers 18 and 20 and pivotably attached thereto. As also shown in FIG. 3, the grid slat retainers 22 and 24 of the lower support plate 14 are provided with spacing elements 32 which maintain the grid slats 28 separated within predetermined limits in the plane of the lower support plate 14.

The separation distance between the pivotably attaching pins 30 of adjacent grid slats 28 is determined in relationship to the separation provided by the spacing elements 32 and the distance from the focal spot 26 to the grid slats 28, such that each of the grid slats 28 is maintained focused on the focal spot 26 of the x-ray source, or stated differently, always points in a direction towards the focal spot.

Figure 4:
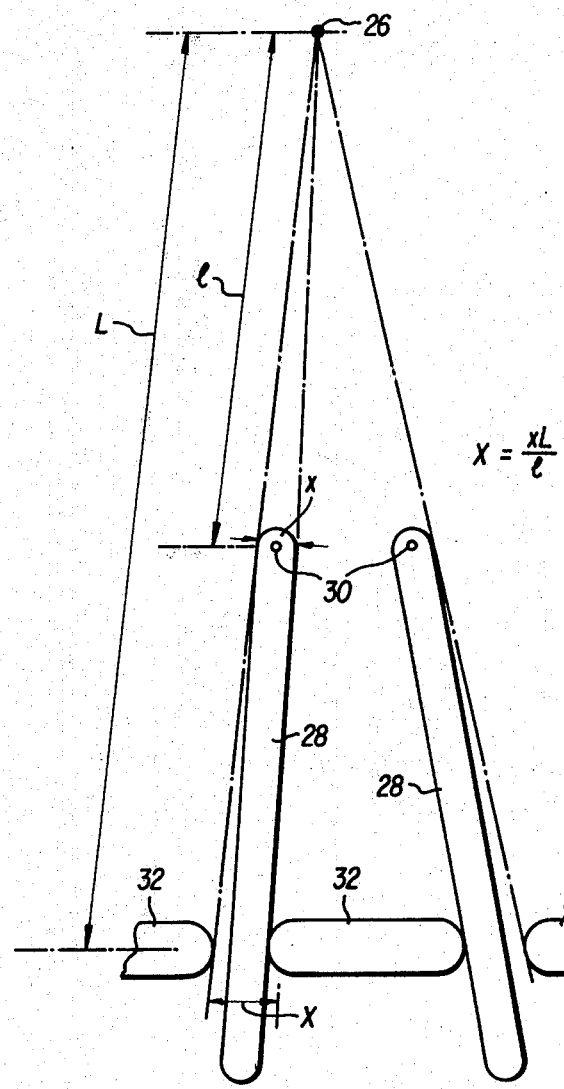
FIG. 4 is a schematic cross-sectional view illustrating the geometrical relationship between the x-ray source focal spot, the grid slats, and the grid slat spacers of the scanning grid apparatus according to the invention.

In FIG. 4, which is a schematic cross-sectional view illustrating the geometrical relationship of the grid slats 28 with respect to the focal spot 26, the pins 30, and the spacing elements 32, it is better seen how the grid slats 28 of the invention are maintained focused on the focal spot 26 of the x-ray source. It is readily understood by inspection that in order to minimize primary radiation cut-off by the grid slats 28, that the separation distance X between adjacent spacing elements 32 should be less than or equal to (xL/l), where x is equal to the width of the individual grid slat 28, L is equal to the distance from the focal spot 26 to the respective spacing elements 32, and l is the distance from the focal spot 26 to the grid slat 28. By so limiting the spacer separation distance X, primary radiation cut-off is effectively limited to the amount of primary radiations blocked by the cross-sectional area of the individual grid slats 28, and is not further effected by travelling movement of the grid slats 28 within the distance X separating adjacent spacing elements 32. Advantageously this facilitates the mechanical rotation of the grid slats 28, since typically the grid slats 28 are not pinched between adjacent spacing elements 32. If the x-ray focal spot to image receptor distance is to be varied then the separation distance X is given also by (xL/l), but where L and l are the shortest distances allowed.

Figure 1:
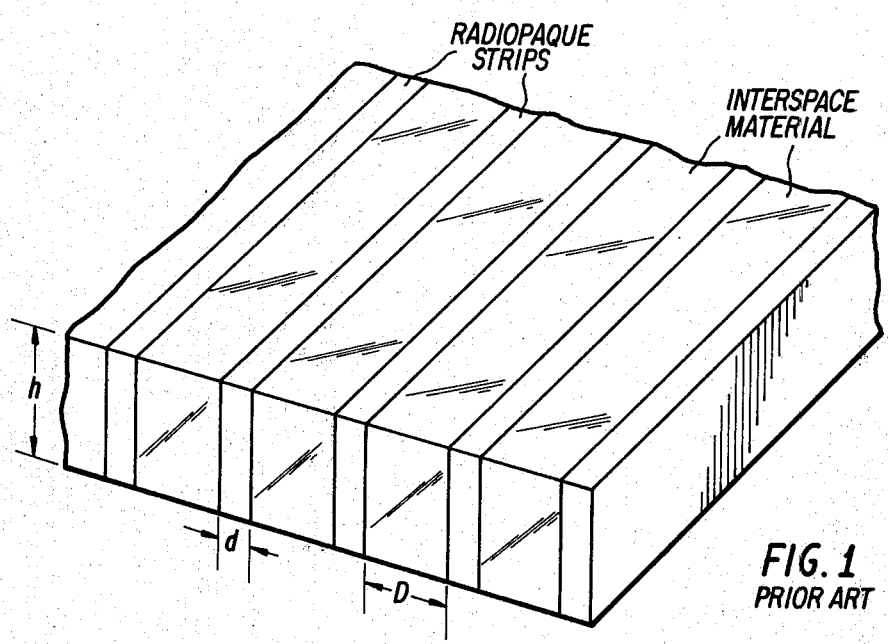
FIGS. 1 and 2 are schematic prospective views of conventional Bucky grids of the prior art.
Figure 2:
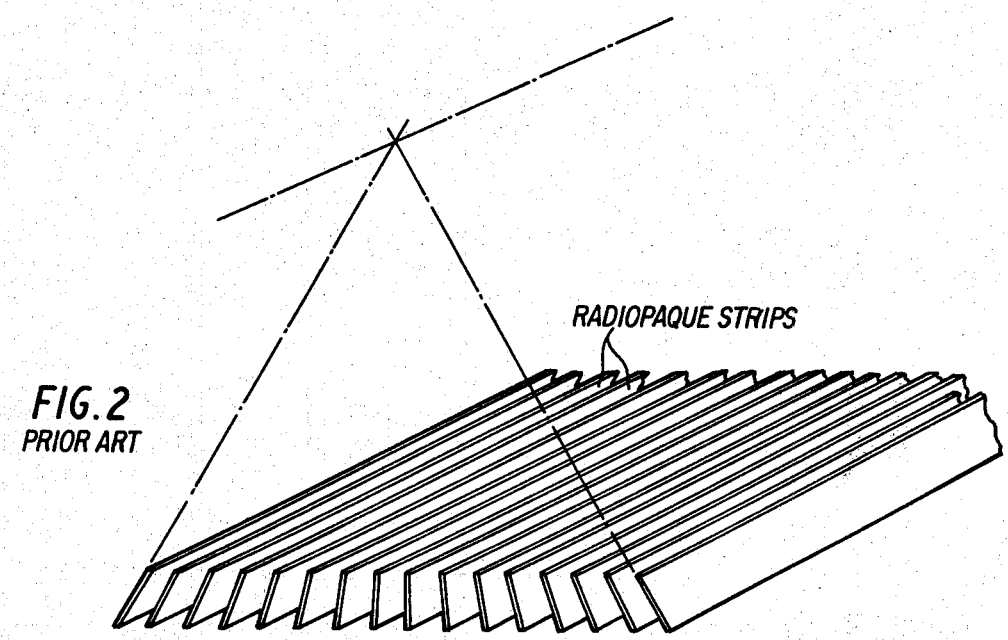

The embodiment shown in FIG. 3 employs thicker radiopaque strips than are conventionally employed in the grids shown in FIGS. 1 and 2 (in the range of from 25 to 75 mils rather than 2 mils), and employ no interspace material other than air between adjacent grid slats 28. The thicker radiopaque grid strips eliminate almost all scatter penetration of the strips (a significant problem in conventional grids) and the lack of interspace material allows for the employment of much higher grid ratios than conventionally used, without any decrease in primary x-rays transmitted through the grid. Thus, the embodiment shown in FIG. 3 allows the employment of very high grid ratios having a high primary and low scattered x-ray transmission.

As shown in FIG. 3, the scanning grid of this embodiment includes the linkage arm 16 which pivots about the focal spot 26 of the x-ray source. The linkage arm 16 is provided with slots 34, 34a, which couples pegs 36 and 38 protruding from the sides of grid slat retainers 20 and 24. During a non-tomographic movement of the x-ray source, i.e. where no movement or scanning of the x-ray source occurs during an exposure, through coupling of the upper and lower support plates 12 and 14 to the linkage arm 16 by means of respective pegs 36 and 38 within slots 34,34a, the upper and lower support plates 12 and 14 undergo a transverse movement perpendicular to the grid slats 28 such that the grid slats 28 pivot about their attachment points on the opposed grid slat retainers 18 and 20 while maintaining focus on the focal spot 26 due to the proportional movement of the lower grid slat retainers 22 and 24, it being understood that the movement of the upper and lower support plates 12 and 14 is restrained to their respective planes by conventional means not shown. Thus, during a stationary exposure, scanning grid 10, according to the invention, moves linearly in the direction of the arrows as indicated in FIG. 3 through a sufficiently large number of grid strip intervals so that the shadows of the grid slats which would otherwise appear on the x-ray sensitive image receptor are blurred out and invisible. Thus, the attachment of the two support plates 12 and 14 to the linkage arm 16 which pivots about the x-ray tube focal spot assures that the grid slats 28 are focused throughout the movement of the support plates 12 and 14, eliminating any grid cut-off. Typically, the grid slats 28 shown in FIG. 3 have a thickness d, separation distance D, and a height h, where d ranges from 25-75 mils, D ranges from 100-500 mils, and h equals 1-5 inches or more.

In the event that the x-ray source is to undergo a tomographic movement in which the subject being irradiated is scanned by the x-ray source in a direction transverse, i.e. orthogonal, to the grid slats of the scanning grid 10 shown in FIG. 3, then the lower support plate 14 can be maintained stationary by conventional means not shown if the x-ray sensitive image receptor is moved a relatively large number of grid slat intervals, e.g. 10-20, thereby assuring blurring of grid slat shadows. Alternatively, in a tomographic movement where the image receptor traverses only a few grid slat intervals, then the retainers 22, 24 are also scanned to assure the requisite blurring of slat shadows. Then the linkage arm 16 is pivoted about a pivot point 40 located along a line that passes through the focal spot and that is parallel to the grid slats as shown in FIG. 3. Locating the pivot point 40 of the linkage arm 16 in such a manner maintains grid focus in alignment when the x-ray source is moved during a tomographic movement, it being understood that in such a movement the source and image receptor move in opposite directions in parallel planes located on opposite sides of the plane of the scanning grid of the invention.

Figure 5:
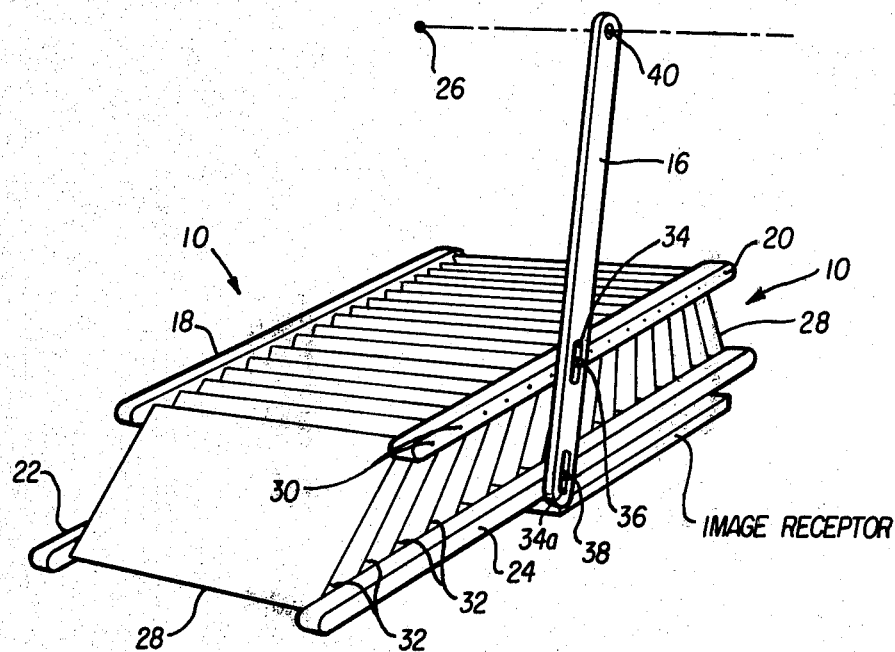
FIG. 5 is a perspective view of a second embodiment of a scanning grid apparatus according to the invention.

In FIG. 5 is shown a perspective view of a linear scanning grid apparatus according to the invention actually constructed and tested. Like the embodiment shown in FIG. 3, the linear scanning grid apparatus according to the invention as shown in FIG. 5 consists of grid slats 28 pivotably supported and attached to opposed grid slat retainers 18 and 20 located in a first plane, with the grid slats 28 maintained separate within predetermined limits in a second plane by means of spacing elements 32 provided on a second pair of opposed grid slat retainers 22 and 24. Once again, during an exposure the grid slats scan the radiation field and their motion is synchronized with the exposure time of the x-ray source so that the image receptor receives a uniform radiation exposure. The grid slats 28 are focused as before, with the distance between the slats established by the spacing elements 32 in the lower opposed grid slat retainers 22 and 24 being the geometrical projection of the separation distance between grid slats established in the opposed upper grid slat retainers 18 and 20. Both pairs 18, 20 and 22, 24 of grid slat retainers as shown in FIG. 5 are likewise connected to a slotted linkage arm 16 by means of respective pegs 20 and 24, which maintains grid slat focus and alignment during a scan. Important design parameters of a prototype linear scanning grid shown in FIG. 5 are listed in Table 1 below, as follows:

TABLE I

| Design Parameters of Prototype Linear Scanning Grid | | | |
|---|---|---|---|
| SID* | 122 cm | Spetal Thickness-lead** | 0.89 mm |
| Grid Ratio | 15.5/1 | Septal Thickness-total** | 1.5 mm |
| Grid Lines | 1.64/cm | Septal Height-lead** | 63.5 mm |
| Lead Content | 10.5 g/cm | Septal Height-totalII | 71.5 mm |
| Magnification+ | 1.13 | | |

*Source-to-Image Receptor Distance
+At tabletop
**Lead speta are attached to steel substrate As suggested in Table I, the grid slats are constructed of a steel substrate to which is laminated at least one lead septum. In this way, mechanical rigidity is provided by the substrate, which also serves to absorb scatter radiation, while the relatively malleable lead septa assure necessary scatter absorption. Typically, lead septa are simply pasted to either one or the other or both sides of the steel substrates. However, the septa can otherwise be sandwiched between a pair of steel substrates. Other x-ray absorbing substrate and septa materials are also possible, but for reasons of economy and availability, steel and lead are preferred.

Preliminary evaluations of the primary and secondary radiation transmission characteristics of the scanning grid shown in FIG. 5 at 100 kVp source operation are compared in Table II to commonly used grids. The details of the measurement techniques employed to obtain the date in Table II is outlined in Barnes et al, "The Design and Performance of a Scanning Multiple Slit Assembly", MED. PHYS. 6:197–204, May/June 1979. The results of Table II indicate that the prototype linear scanning grid according to the invention is superior to the commonly used grids. The primary transmission of the prototype linear scanning grid is comparable to that of the lower ratio 8/1 grid, while the scatter transmission thereof is markedly less than the 16/1 grid.

TABLE II

Comparison of the Primary and Scatter Transmission of Scanning and Commonly Used Grids

| Grid | % Primary Transmission* | % Scatter Transmission* |
|---|---|---|
| 8/1, 31.5 lines/cm+ | 67 | 11.2 |
| 8/1, 41.3 lines/cm** | 66 | 11.4 |
| 12/1, 31.5 lines/cm+ | 60 | 6.4 |
| 16/1, 31/5 lines/cm+ | 56 | 4.2 |
| Scanning Grid | 67 | 3.7 |

*Measured at 100kVp, 3φemploying an 18 cm thick, 30 cm × 30 cm Lucite phantom
+Fiber interspace grids with lead contents of 363, 572 and 765 mg/cm²
**Aluminum interspace grid with a lead content of 360 mg/cm²

Figure 6:
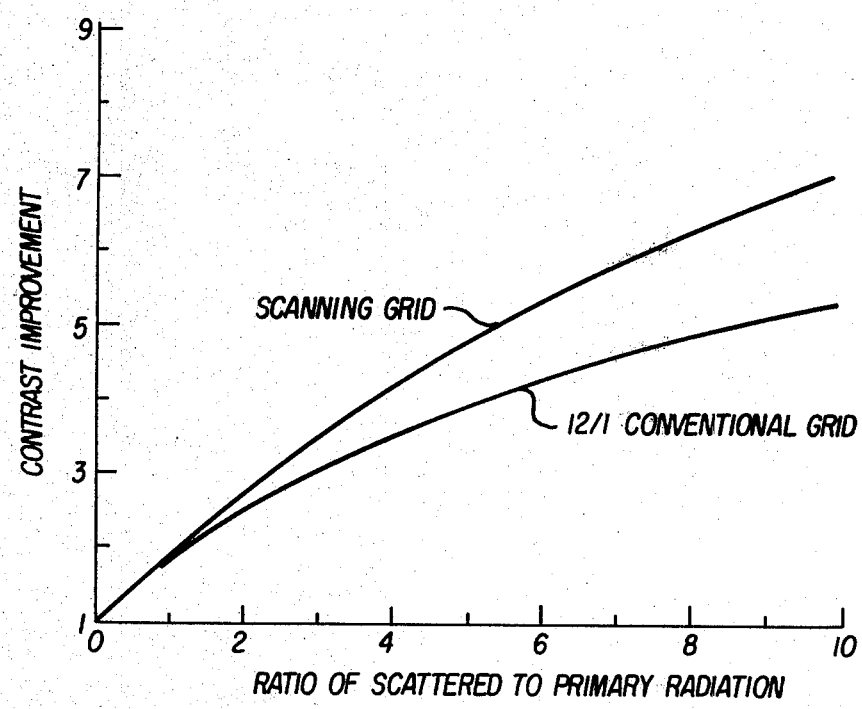
FIG. 6 is a graph illustrating the improved contrast in the radiographic image achieved by a prototype scanning grid apparatus according to the invention in comparison to that of a conventional grid.

The contrast improvement obtained with an anti-scatter technique depends on the relative amount of scatter emerging from the patient and is given by:

$$\text{Contrast Improvement} = SDF'/SDF, \quad (1)$$

where SDF' and SDF is the scatter degradation factor with and without the scatter reduction method. The SDF is the fraction of primary beam or possible contrast imaged due to the presence of scatter and is equal to:

$$SDF = (1 + S/P)^{-1} \quad (2)$$

where S/P is the ratio of scattered-to-primary radiation imaged. Employing Eqns. (1) and (2) and the results tabulated in Table II, one can determine the contrast improvement obtained with the scanning and commonly used grids as a function of S/P. This is plotted for the scanning and conventional 12/1 grid in FIG. 6 and illustrates that significant improvements in contrast over conventional grids should be obtained with the scanning grid for large S/P ratios. Such improvements have been observed in practice.

The reasons why a scanning grid is superior to a conventional grid are: (1) there is no scatter penetration of the relatively thick grid septa; and (2) there is no interspace material. The lack of scatter septal penetration results in a decreased scatter transmission for a given grid ratio while the air interspace results in a primary transmission that, for a given number of grid lines per cm, is independent of grid ratio. The current performance of the prototype scanning grid could be improved by employing thinner lead septa (~0.1–0.2 mm), a higher grid ratio, and wavy rather than linear grid slats as further discussed hereinafter. Employing thinner lead septa would increase the device's primary transmission while the latter two modifications would decrease its scatter transmission.

For a linear scanning grid with no septal penetration scatter solid angle considerations indicate that the transmission of scatter is given by the expression:

$$T_s \simeq \frac{2}{\pi} \tan^{-1}\left(\frac{1}{r}\right), \quad (3)$$

where r is the grid ratio as defined previously. Eqn. (3) indicates that the greater the grid ratio the smaller the fraction of scatter transmitted by the grid. Eqn. (3) predicts a scatter transmission of 4.1% for the linear scanning grid of Table I and a value of 3.7% was measured. For crossed linear scanning grids the scatter transmission is given by:

$$T_s \simeq \left[\frac{2}{\pi} \tan^{-1}\left(\frac{1}{r_1}\right)\right]\left[\frac{2}{\pi} \tan^{-1}\left(\frac{1}{r_2}\right)\right], \quad (4)$$

where $r_1$ and $r_2$ are the grid ratios of the first and second grids. A scanning grid employing wavy grid slats also suppresses scatter in two dimensions and its scatter transmission is given by:

$$T_s \simeq \left[\frac{2}{\pi} \tan^{-1}\left(\frac{1}{r}\right)\right]\left[\frac{2}{\pi} \tan^{-1}\left(\frac{1}{r_t}\right)\right], \quad (5)$$

where r is the grid ratio along the scanning direction and $r_t$ is the effective ratio transverse to the scanning direction. $r_t$ is given to first order by the height of slats (h) divided by the average distance ($\overline{D}$) between slats transverse to the scanning direction.

The primary transmission of a scanning grid, because of the lack of interspace material, is simply the ratio of interspace area to total area and is given for a linear and wavy arrangement by:

$$T_p = D/(d+D) \quad (6)$$

where d and D are as defined previously, while for crossed linear grids the primary transmission is given by:

$$T_p = \left[\frac{D}{d+D}\right]^2 \quad (7)$$

Eqns. (3)–(5) are approximate expressions since they assume that the scattering medium is infinite in extent and that the scatter emerging from the bottom of the scattering medium on the patient is isotropic. However, they agree with the general trends observed in practice and along with Eqns. (6) and (7) indicate how the performance of different embodiments of the scanning grid depends on design parameters. For example, for a wavy scanning grid with d=40 mil, D=200 mil, h~1.5 inches, and $\overline{D}$=400 mil, Eqn. (6) indicates a primary transmission of 83% and Eqn. (5) indicates a scatter transmission of ~1.4%. If h is increased to 3 inches the scatter transmission would be reduced to ~0.4% and the primary transmission would remain unchanged. Such a grid would be a vast improvement over the conventional grids in Table II and would virtually eliminate scattered x-rays while transmitting most of the information carrying primary x-rays.

Figure 7A:
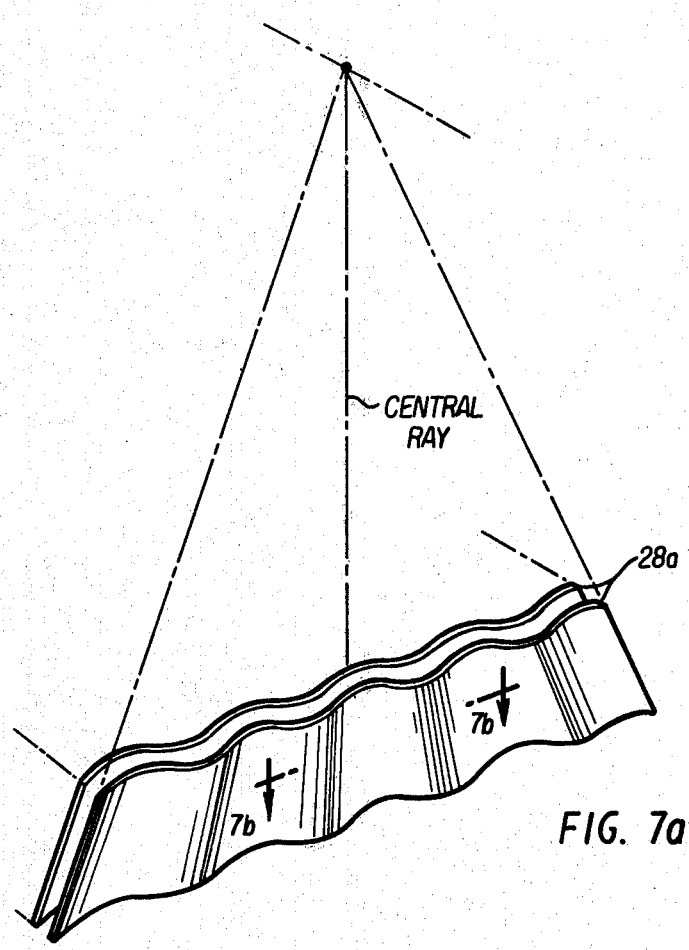
FIG. 7a is a schematic perspective representation of a scanning grid apparatus according to the invention employing wavy grid slats.
Figure 7B:
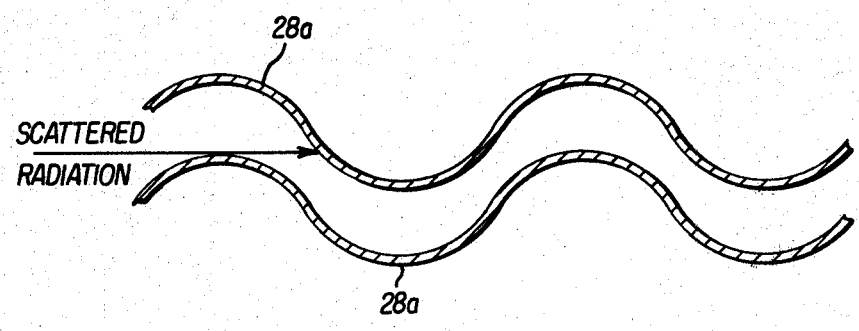

FIG. 7a illustrates schematically a scanning grid implementation according to the invention employing wavy grid slats 28a rather than linear grid slats 28 in order to further improve scatter suppression capabilities. A wavy grid slat array, the concept of which, it should be understood, also includes zigzag, trapezoidal, triangular, or other similar slat patterns, is superior for scatter suppression since x-rays scattered parallel to the grid slats in the linear arrangement have a high probability of being absorbed by the wavy grid slats. That is, the effective solid angle from which scattered x-rays can originate as seen by a point on the image is less for a wavy arrangement than for a linear arrangement. It is important to note that due to the divergence of the x-ray beam and height of the grid slats, the wavy pattern of the grid slats 28a also diverges relative to the x-ray source focal spot 26, as shown in FIG. 7a. Scatter suppression is best minimized by intermeshing adjacent wavy grid slats 28 at least slightly, such that no direct unobstructed scatter path exists between adjacent wavy grid slats 28a, as shown in FIG. 7b.

Figure 8:
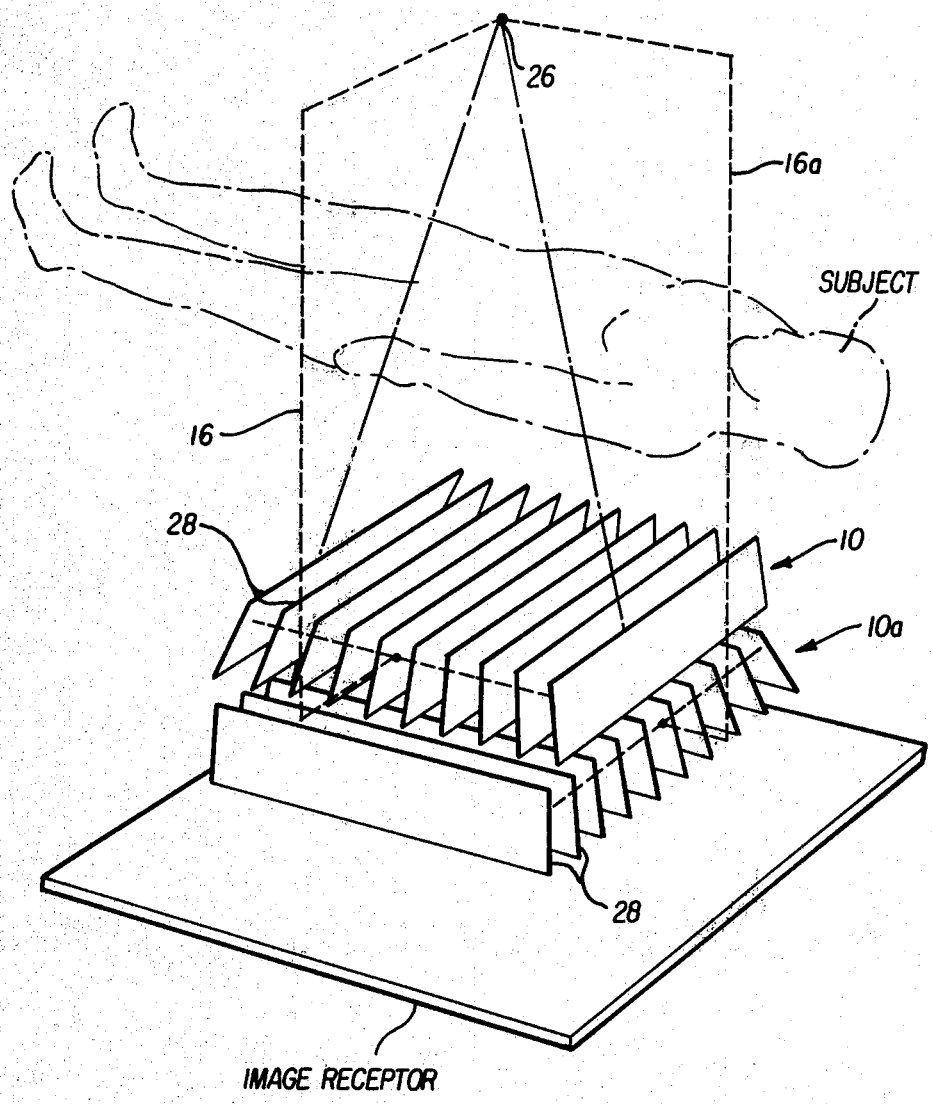
FIG. 8 is a schematic perspective view of an alternative embodiment of a scanning grid apparatus according to the invention employing orthogonally arranged scanning grids mechanically coupled to the focal spot of the x-ray source.

In an alternative embodiment also designed to maximize secondary scatter absorption, a scanning grid apparatus is provided employing, in addition to a scanning grid 10 of the type noted above, a second scanning grid 10a arranged orthogonally with respect to the scanning grid 10, such that the grid slots 28 of the second scanning grid 10a are arranged generally perpendicular to the grid slats 28 of the scanning grid 10, as shown schematically in FIG. 8. In this embodiment, each of the scanning grids 10 and 10a are coupled, as is schematically shown, to the focal spot 26 of the x-ray source and are adapted to provide orthogonal scanning movements in a manner as described above.

Obviously, numerous modifications and variations of the present invention are possible in light of the above teachings. For example, although primary x-ray radiation cut-off is minimized by pivotably attaching the grid slats of the scanning grid of the invention to the grid slat retainers closest to the subject being irradiated, it is possible to pivotally attach the grid slats to either of the pairs of grid slat retainers while providing the requisite spacing elements in the other pair of grid slat retainers. Also, the coupling of the grid slat retainer support plates to the focal spot can be accomplished by means other than a mechanical linkage arm. Alternatively, a hydraulic coupling arrangement can readily be implemented, or an electronic coupling system using stepping motors keyed to source movement is possible. It is therefore to be understood that within the scope of the appended claims, the invention may be practiced otherwise than as specifically described herein.

What is claimed as new and desired to be secured by Letters Patent of the United States is:

1. A scanning grid apparatus exhibiting high primary and low secondary x-ray transmission of x-ray radiation, said apparatus adapted to be positioned between an x-ray source defining a focal spot and an x-ray sensitive image receptor such that x-rays emitted from said source pass through a subject and through said grid apparatus to said receptor, comprising:
   at least one scanning grid comprising,
   a first pair of opposed longitudinally extending grid slat retainers,
   a second pair of opposed longitudinally extending grid slat retainers, said pairs of grid slat retainers disposed in parallel planes with said first pair adapted to be located between said subject and said second pair,
   a plurality of radiopaque grid slats pivotably attached at pivot points at predetermined intervals between the retainers of one of the pairs of said grid slat retainers, and
   means for scanning said grid slats by moving at least one of said pairs of retainers longitudinally in a direction transverse to said plural grid slats and for maintaining said grid slats focused on said focal spot during said scanning, comprising,
   means for coupling at least said one pair of retainers having said pivot points to said focal spot and for moving said at least said one pair longitudinally in a direction transverse to said grid slats, and
   the other pair of said retainers to which said grid slats are not pivotably attached comprising spacing means for maintaining said grid slats separated predetermined distances within predetermined limits in the plane of said other pair of retainers, said predetermined intervals between said pivot points and the separation distances between slats along the other retainer pair selected to maintain focus of each of said slats on said focal spot during movement of said at least one pair of retainers by said coupling means.

2. A scanning grid apparatus according to claim 1, further comprising:
   said grid slats pivotably attached to said first pair of retainers; and
   said second pair of retainers including said spacing means.

3. A scanning grid apparatus according to claim 1, adapted to be used in conjunction with a stationary x-ray source, further comprising:
   said coupling means comprising means for longitudinally moving said second pair of retainers a distance proportional to the longitudinal movement of said first pair of retainers.

4. A scanning grid apparatus according to claim 3, wherein said couping means comprises:
   said first and second pairs of retainers provided with respective coupling pegs; and
   a linkage arm pivoted along a line passing through the focal spot, said line parallel to said grid slats, said arm having slots coupling said pegs of said pairs of retainers such that pivotal rotation of said arm produces the longitudinal movement of the first and second pairs of retainers.

5. A scanning grid apparatus according to claim 1, adapted to be used in conjunction with an x-ray source and an x-ray sensitive receptor undergoing a tomographic movement, wherein said coupling means comprises:
   means for maintaining said second pair of retainers stationary during said tomographic movement,
   said first pair of retainers having a coupling peg, and
   a linkage arm coupled to said source and pivoted along a line passing through the focal spot, said line parallel to said grid slats, said arm having a slot coupling said peg such that tomographic movement of said source produces the longitudinal movement of the first pair of retainers.

6. A scanning grid apparatus according to claims 1, 2, 3, 4 or 5, further comprising:

each of said grid slats having a wavy cross-section with the period of the waves diverging from the first pair of retainers to the second pair of retainers in convergence on said focal spot.

7. A scanning grid apparatus according to claim 6, further comprising:
said wavy grid slats intermeshed to obstruct x-ray scatter radiation having components parallel to the plane of said grid slats.

8. A scanning grid apparatus according to claim 1, wherein the predetermined limits within which said grid slats are maintained separated by said spacing means is defined by the following relationship:

$$X < xL/l$$

where X corresponds to said predetermined limits, x is the slat thickness, L is the distance from the source focal spot to the spacing means, and l is the distance from the source focal spot to the pivot points of said grid slats.

9. A scanning grid apparatus according to claim 1, wherein at least one of said grid slats comprises:
a mechanically rigid substrate; and
at least one x-ray absorbing septum laminated to said substrate.

10. A scanning grid apparatus according to claim 9, further comprising:
said substrate formed of steel; and
said septum formed of lead.

11. A scanning grid apparatus according to claims 1, 2, 3, 5, 8 or 9 further comprising:
a second scanning grid adapted to be positioned between said subject and said image receptor, said second scanning grid identical to said at least one scanning grid and having the grid slat retainers thereof disposed orthogonal to the grid slat retainers of said at least one scanning grid.

* * * * *